United States Patent [19]

Stec, III et al.

[11] Patent Number: 5,824,806
[45] Date of Patent: Oct. 20, 1998

[54] PROCESSES FOR PREPARING TNAZ

[75] Inventors: Daniel Stec, III, Hackettstown; Ralph L. Perez, Ogdensburg; Paritosh R. Dave, Bridgewater, all of N.J.; Thomas G. Archibald, Fair Oaks, Calif.

[73] Assignee: The United States of America as represented by the The Secretary of the Army, Washington, D.C.

[21] Appl. No.: 440,946

[22] Filed: May 15, 1995

[51] Int. Cl.⁶ .................................................. C07D 203/22
[52] U.S. Cl. ............................................................ 548/953
[58] Field of Search ............................................... 548/953

[56] References Cited

U.S. PATENT DOCUMENTS 5,336,784  8/1994  Hiskey et al. ......................... 548/953
5,395,945  3/1995  Hiskey ................................... 548/953

*Primary Examiner*—Jacqueline Haley
*Attorney, Agent, or Firm*—John Moran; Michael Sachs; John E. Callaghan

[57] ABSTRACT

TNAZ can be prepared directly from N-tertiarybutyl-3,3-dinitroazetidine compounds. The compounds may be in the form of the tertiary amine or the quaternary amine. The reaction is in the presence of acetic anhydride and nitrate ions. It gives high yields and uses mild conditions.

13 Claims, 4 Drawing Sheets

5,824,806

PROCESSES FOR PREPARING TNAZ

STATEMENT OF GOVERNMENT INTEREST

The invention described herein may be manufactured, used and licensed by or for the United States Government for governmental purposes without the payment to us of any royalties thereon.

STATEMENT OF RELATED APPLICATIONS

This application is related to the U.S. Patent Applications described below; the applications have been filed simultaneously with this application. The applications are:

DAR 4-94A Ser. No. 08/440,947 filed May 15, 1995 allowed

DAR 4-94C Ser. No. 08/440,945 filed May 15, 1995 pending

DAR 4-94D Ser. No. 081441,511 filed May 15, 1995 (U.S. Pat. No. 5,580,98/)

DAR 4-94E S.N 08/441,512 filed May 15, 1995 pending

BACKGROUND OF INVENTION

This invention relates to processes for marking azetidines, particularly 1,3,3-trinitroazetidine. Generally, the field of energetic materials use compounds having N-Nitro, C-Nitro and O-Nitro structures. A material under current evaluation is 1,3,3-trinitroazetidine, known at TNAZ. This has a high energy density and other properties which are of importance in explosives and propellants. Although it has valuable chemical and physical properties for use as an energetic material, the present processes for making it are of poor yield. They use N-acetyl 3,3-dinitroazetidine as a starting material. The reaction conditions lead to many side reactions and ring openings which give low yields and difficult purifications. The present invention provides processes that produce TNAZ in relatively high yields and under relatively mild conditions.

SUMMARY OF INVENTION AND FIGURE

Overall, the processes of this invention for preparing TNAZ are advantageous in that the reaction conditions give improved yields and readily recoverable products. This invention can use N-tertiary butyl, 3,3-dinitroazetidine or its quatenary salt as a starting material and can control the reactions so that TNAZ is produced in high yield. Generally the reaction will proceed in the presence of acetic anhydride and either a proton or a quaternary salt of the azetidine to form the TNAZ.

BRIEF DESCRIPTION OF DRAWINGS

The FIG. 1. illustrates several processes of the invention that produce TNAZ.

DETAILED DESCRIPTION OF THE INVENTION AND FIGURE

Figure 1A:
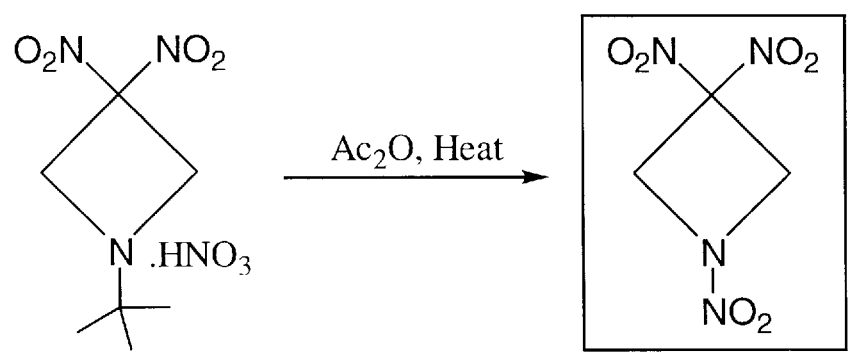
Figure 1B:
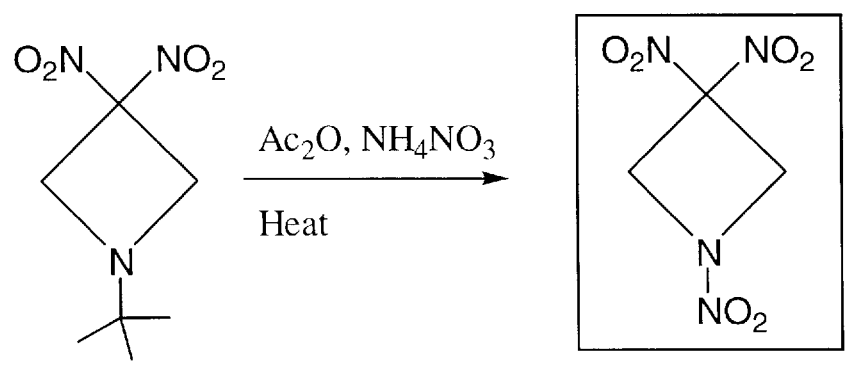
Figure 1C:
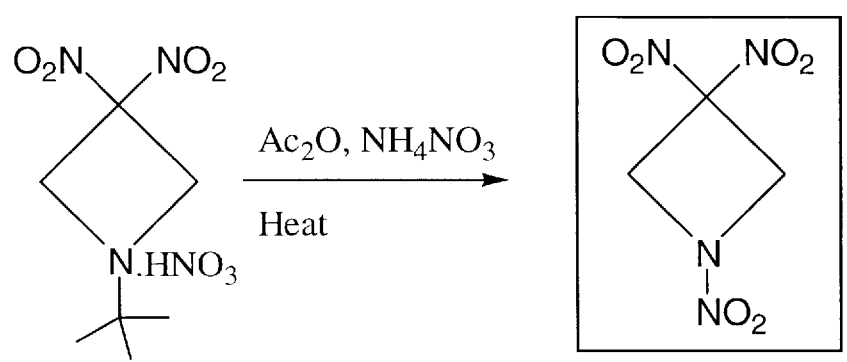
Figure 1D:
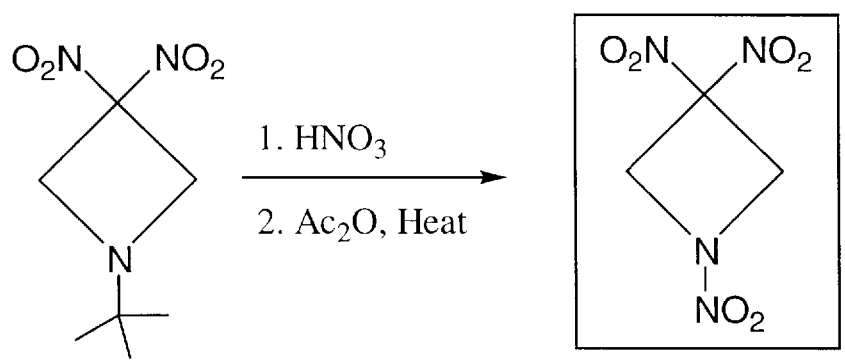

The practice of the invention and the processes and reaction conditions of the steps of the invention are further described by reference to the following detailed description.

As shown in the FIGURE, the reaction uses N-tertiarybutyl,3,3-dinitroazetidine, TBDNA, as a starting material. The TBDNA can be used as the tertiary amine or it can be quarternized to the azetidinium salt. The TBDNA is reacted with a source of protons and acetic anhydride. It appears that the reaction proceeds by a mechanism which involves the elimination of the tertiary butyl substituent, the formation of a protonated secondary amine nitrate at the aza nitrogen and the dehydration of the nitrate to leave the nitro group at the aza nitrogen and thus provide the TNAZ.

In one embodiment of the process, shown as (a) in the FIGURE, the TBDNA is reacted with nitric acid to form the quaternary salt, ANS; the ANS is reacted in the presence of acetic anhydride to provide the TNAZ. In a second embodiment, shown as (b) in the FIGURE, TBDNA is reacted with a mixture of ammonium nitrate and acetic anhydride to from the TNAZ. In a third embodiment, shown as (c), the quaternary salt, ANS, is reacted with a mixture of ammonium nitrate and acetic anhydride to produce TNAZ. A fourth embodiment, shown as (c), is the reaction of the TBDNA with a mixture of nitric acid and acetic anhydride.

The reaction conditions are relatively mild. The temperature range of about 65 to about 75 degrees C. is preferred. At this temperature, the reaction time will be about 6 to about 8 hours. While higher temperatures can shorten the reaction times, product loss and discoloration occurs as the temperature is increased. The mol ratio of acetic anhydride to azetidine is in the range of about 2.8 to about 22; the minimum amount of acetic anhydride is an amount sufficient to, make a slurry, a preferred amount is about 4–6 equivalents. The mol ratio of nitrate ions to azetidine is up to about 1.9; the minimum ratio is one equivalent and 1.5 has been satisfactory.

EXAMPLE

TBDNA, Ammonium Nitrate, Acetic anhydride

TBDNA is reacted with ammonium nitrate and acetic anhydride to produce TNAZ. Acetic anhydride (61 ml., 8.8 mol equiv.) is added to TBDNA (14.8 gm). Ammonium nitrate (8.8 gm., 50% excess over free base) is added with stirring and the reaction mixture is heated. The reaction temperature was maintained between 75–80 degrees C. After 90 minutes, a light green color developed that gradually faded to yellow brown color. Samples were taken at 100 and 225 minutes and showed formation of TNAZ. After; 260 minutes, heating was stopped. A 20 ml. aliquot was added to 20 ml. of water and the two layer mix was stirred. Solids formed in 40 minutes. The mixture was stirred overnight and filtered. The filtrate was washed with a small amount of water and dried. TNAZ was obtained as a white solid ( 2.3 g, m.p. 96–98 degrees C.). NMR (2°–13° C.) showed TNAZ with very little PIB and no nitroso compounds. The crude yield of TNAZ was 61%.

EXAMPLE

ANS and Acetic Anhydride

A salt is prepared by the reaction of TBDNA with nitric acid. The salt is N-tertbutyl,3,3-dinitroazetidinium nitrate, ANS.

The only reactants are ANS and acetic anhydride. The ANS partially dissolves in warm anhydride. The reaction system is dynamic: as the reaction proceeds, ANS forms TNAZ and more ANS dissolves to react and form more TNAZ. The molar ratio of anhydride to ANS is in the range of about 3.4 to about 20. The reaction does not have to be under an inert atmosphere and no special precautions were required against moisture.

If the temperature is too high, for example, a reactor wall temperature in excess of 80 degrees C., an unwanted decomposition of ANS occurs. It goes to acetyl nitrates which decomposes with a tell-tale blue green color. At the high temperatures, the reaction will stop at about 60–70% conversion with about 35–25% TBDNA present. The color change to blue-green indicates that the reaction needs to be redone.

The formation of acetic acid does not affect the reaction. Acetic acid was added to the reactor without any harmful effect. The optimum internal temperature range is about 74 to about 75 degrees C. and the reaction time was 6 to 8 hours. After the reaction was stopped, the TNAZ product was recovered by treating the oily residue with aqueous sodium bicarbonate and filtration of the solids. The solids were stirred with 10% nitric acid to remove any TBDNA and the purified TNAZ was obtained.

It can be seen that the proton may be from a prdtic acid, $HNO_3$, or a salt ANS. The nitrate ion may be from nitric acid or from a nitrate salt. The process of the invention gives good process control and good yields of TNAZ. The ANS can also be used as a heat sink to moderate the temperature during the course of the reaction.

It is intended that the invention includes the equivalent compounds, products, reaction conditions, reaction steps, reaction processes and variations of such equivalents as are commonly practiced in this field as well as the specific embodiments described above.

We claim:

1. A process for preparation of 1,3,3-trinitroazetldine which comprises the step of reacting a N-terirtiarybutyl,3,3-dinitroazetidine compound in the presence of acetic anhydride and nitrate ions to eliminate the tertiarybutyl substituent while forming a protonated secondary amine nitrate of the azetidine and dehydrating the nitrate to yield the 1,3,3-trinitro azetidine, the N-tertiarybutyl,3,3-dinitroazetidine compound being selected from (1) its quaternary form and (2) the reaction product of its tertiary amine form and protons.

2. The process of claim 1 wherein the N-tertiarybutyl,3,3-dinitroazetidine compound is the nitrate salt of N-tertiarybutyl,3,3-dinitroazetidine.

3. The process of claim 1 wherein the N-tertiarybutyl,3,3-dinitroazetidine compound is N-tertiarybutyl,3,3-dinitroazetidine.

4. The process of claim 1 wherein the reactants include ammonium nitrate.

5. The process of claim 1 wherein the nitrate salt of N-tertiarybutyl,3,3-dinitroazetidine is reacted in the presence of acetic anhydride.

6. The process of claim 1 wherein the nitrate salt of N-tertiarybutyl,3,3-dinitroazetidine is reacted in the presence of acetic anhydride and ammonium nitrate.

7. The process of claim 1 wherein N-tertiarybutyl,3,3-dinitroazetidine is reacted with acetic anhydride in the presence of nitric acid.

8. The process of claim 1 wherein N-tertiarybutyl,3,3-dinitroazetidine is reacted with acetic anhydride in the presence of ammonium nitrate.

9. The process of claim 1 wherein the reaction temperature is in the range of about 65 to about 75 degrees C.

10. The process of claim 1 wherein the mol ratio of acetic anhydride to azetidine is about 2.8 to about 22.

11. The process of claim 1 wherein the mol ratio of nitrate ions to azetidine is up to about 1.9.

12. A process for preparation of 1,3,3-trinitroazetidine which comprises the step of reacting a quaternary N-tertiarybutyl,3,3-dinitroazetidine in the presence of acetic anhydride and nitrate ions to eliminate the tertiary butyl substituent while forming a protonated secondary amine nitrate of the azetidine and dehydrating the nitrate to yield the 1,3,3-trinitroazetidine.

13. A process for preparation of 1,3,3-trinitroazetidine which comprises the step of reacting N-tertiarybutyl,3,3,-dinitroazetidine and a proton in the presence of acetic anhydride and nitrate ions to eliminate the tertiarybutyl substituent while forming a protonated secondary amine nitrate of the azetidine and dehydrating the nitrate to yield the 1,3,3-trinitroazetidine.

* * * * *